(12) United States Patent
Gittleman (10) Patent No.: US 6,508,650 B2
(45) Date of Patent: Jan. 21, 2003

(54) WINGED IMPRESSION CAP FOR REDUCED HEIGHT DENTAL IMPRESSION POST

(76) Inventor: Neal B. Gittleman, 14 Greenway Plaza #28E, Houston, TX (US) 77046

( * ) Notice: Subject to any disclaimer, the term of this patent is extended or adjusted under 35 U.S.C. 154(b) by 0 days.

(21) Appl. No.: 09/828,593

(22) Filed: Apr. 6, 2001

(65) Prior Publication Data

US 2002/0127515 A1 Sep. 12, 2002

Related U.S. Application Data

(63) Continuation-in-part of application No. 09/309,477, filed on May 10, 1999, now Pat. No. 6,213,773.

(51) Int. Cl.⁷ .............................................. H61C 13/225
(52) U.S. Cl. ........................................ 433/172; 433/214
(58) Field of Search ................................ 433/172, 173, 433/174, 213, 214

(56) References Cited

U.S. PATENT DOCUMENTS 5,133,662 A * 7/1992 Metcalfe ..................... 433/169
5,688,123 A * 11/1997 Meiers et al. ................ 433/173
5,704,788 A * 1/1998 Milne .......................... 433/173
5,779,477 A * 7/1998 Boss ........................... 433/172

* cited by examiner

Primary Examiner—Nicholas D. Lucchesi
Assistant Examiner—Melba Bumgarner
(74) Attorney, Agent, or Firm—Ezra L. Schacht (57) ABSTRACT

An apparatus and method comprised of dental implant impression mounting hardware with a non-interfering, low profile for making time saving and accurate, simultaneous upper and lower impressions and bite registration, with the mouth completely closed and the jaw accurately positioned in centric closure. A low-profile, impression post is snapped within a matching low profile, winged and perforated impression cap held securely within a self-curing elastomeric impression material. The cured impression material retains the low profile impression cap which snaps free of the mating low profile impression alignment post. The impression post is removed and attached to an analog of the permanent endo-osseal implant and snapped back into low profile impression cap embedded in the elastomeric mold. This low profile assembly prevents interference with the taking of a simultaneous upper and lower elastomer impression of the accurately interdigitated jaw using a 'triple tray' while insuring excellent registration.

2 Claims, 9 Drawing Sheets

Figure 1
Prior Art

**Figure 2
PRIOR_ART**

WINGED IMPRESSION CAP FOR REDUCED HEIGHT DENTAL IMPRESSION POST

OTHER APPLICATIONS INCORPORATED HEREIN BY REFERENCE

This Application is a C.I.P. of Ser. No. 09/309,477 filed on May 10, 1999 now U.S. Pat. No. 6,213,773 now allowed.

BACKGROUND OF THE INVENTION

In the field of dental implants, patient comfort and the efficient use of a dentist's time are paramount. Likewise, precision alignment of the prosthetic components is essential. The need to match both natural and artificial, upper and lower teeth to within 5 microns and provide accurate mating of the prosthesis with existing teeth requires accurate replication of oral structures when making dental impressions. To create these accurate models and the final prosthesis, a matched upper and lower impression can be obtained simultaneously with the jaw in the closed position and the teeth in the interdigitated position (centric occlusion). Currently, the impression transfer posts used to register the implants to the upper and lower jaws prevent the full closure of the mouth while making the simultaneous upper and lower impressions. The present invention remedies this oversight.

Existing practice has been to perform the following procedures. After dental implants have healed into the underlying bone structures of the mandible or maxilla and the soft gum tissue has healed, a full set of upper and lower impressions of the mouth are made using individual full or partial arch upper and lower trays. Positive casts of these impressions are mounted upon a mechanical articulator that mimics the motion of the temporo-mandibular joint (tmj). A separate bite registration cast is also made. These positive casts are equipped with accurately placed implant fixture analogs positioned to accurately replicate the structures in the mouth. These positive casts are tested against the bite registration cast.

To make an accurate impression, the healing caps are removed from one or more dental implant fixtures and impression transfer posts are accurately placed with retaining screws on each implant fixture. An impression tray filled with a self-hardening elastomeric impression material is pressed over the region of the dental arch containing the impression transfer posts.

After a few minutes, the elastomeric impression material has set and the impression is removed with a gentle parting pressure. The impression transfer post snaps from its positive detent within the impression material. Then the impression transfer post is unscrewed from the implant and attached to an implant analog with the screw. The healing cap replaced on the dental implant. Now the analog of the dental implant is accurately attached to the impression transfer post which was snapped back into the elastomeric impression material. The same procedure is followed for the opposing dental arch. A third, bite registration impression is taken without the impression transfer posts installed and the teeth in centric closure.

A stone model of the mouth structure with the dental implant analog exactly aligned and retained is created from the separate impressions. These models are combined upon an articulator mimic the actual jaw motions. A model of the final prosthesis is built up and tried in for a non-interfering, good fit. This model relying upon properly placed dental implant analogs cast in the properly aligned position is used to build the final prosthesis.

In, in order quickly to make an accurate, simultaneous impression of the upper and lower teeth in the correct alignment uses a 'triple tray.' This tray consists of a molded plastic assembly with a handle connected to a set of confining dams and a thinopen screen mesh. The mesh is oriented horizontally and is to be placed between the mating occlusal surfaces of the teeth while the jaw is in the closed or centric position. The buccal and lingual dams are molded to the mesh. A paste of quick-setting elastomer is placed on both sides of the mesh within the confines of the dams. The mouth is closed with the upper and lower teeth in the closed or centric position while imbedded within the curing elastomer. In this manner, a matching set of aligned upper and lower impressions along with the proper bite registration are made.

The elastomeric impression materials, such as polyvinylsiloxane or polyether, are dimensionally stable, but need adequate surface area in contact with the impression transfer post to ensure accurate replication of the implant within the models mounted upon the articulator. Currently, long tapered impression transfer posts are used, which have adequate surface area to accurately register the elastomeric impression to the dental implant analog, but interfere with the taking of a single, timesaving, triple tray impression. The height of these anchor posts prevents the quick and accurate use of a time saving triple tray when making simultaneous, closed jaw, upper and lower impressions.

Instead of taking three time-consuming, separate impressions of the upper arch, lower arch and bite registration, a single impression is formed, thus, the 'triple tray' name. If a single area of the partially edentulous mouth is being modeled, a half-arch, triple tray can be used.

Figure 1:
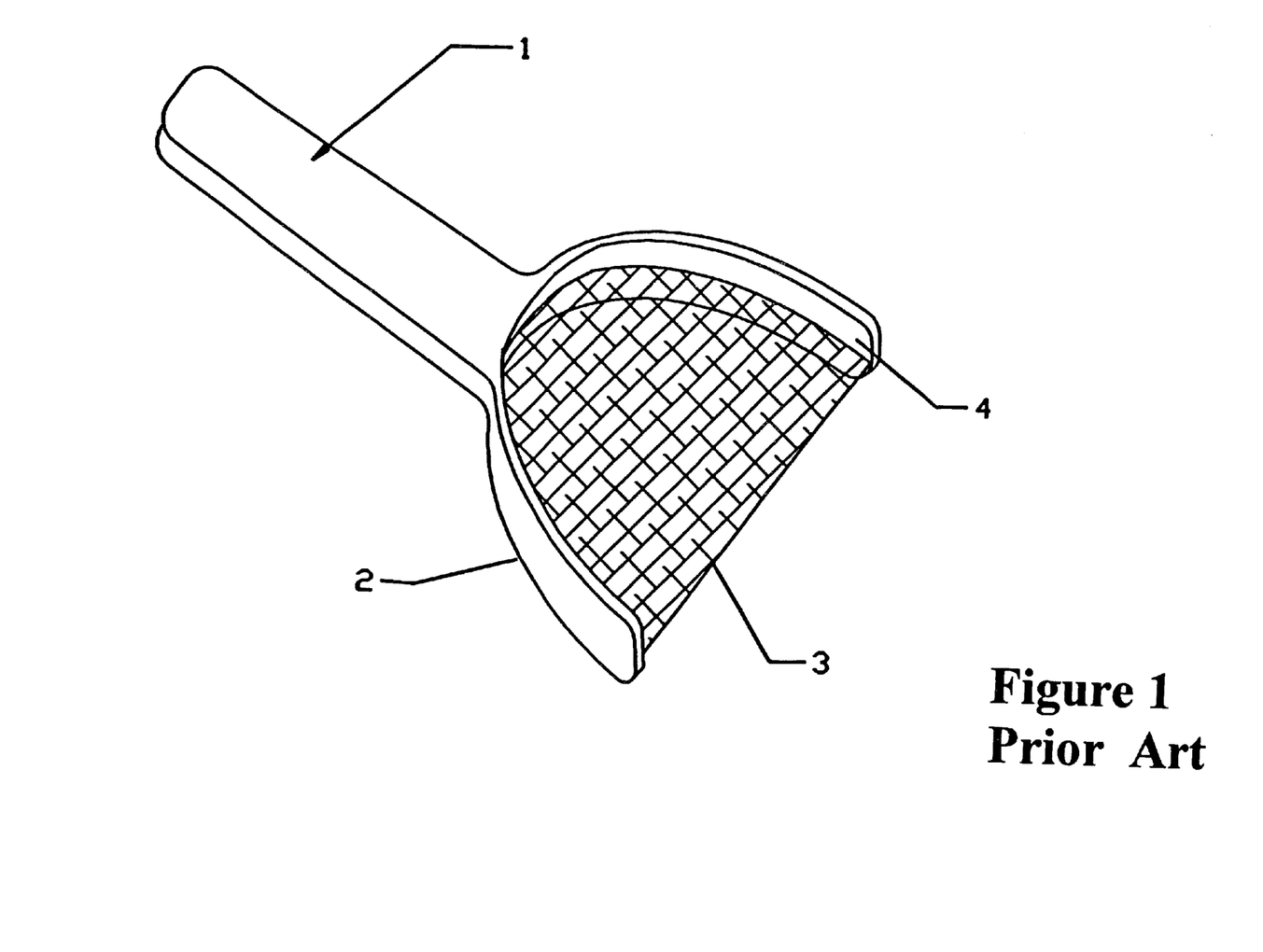
FIG. 1 (prior art) details a perspective view of an anterior triple tray.
Figure 2:
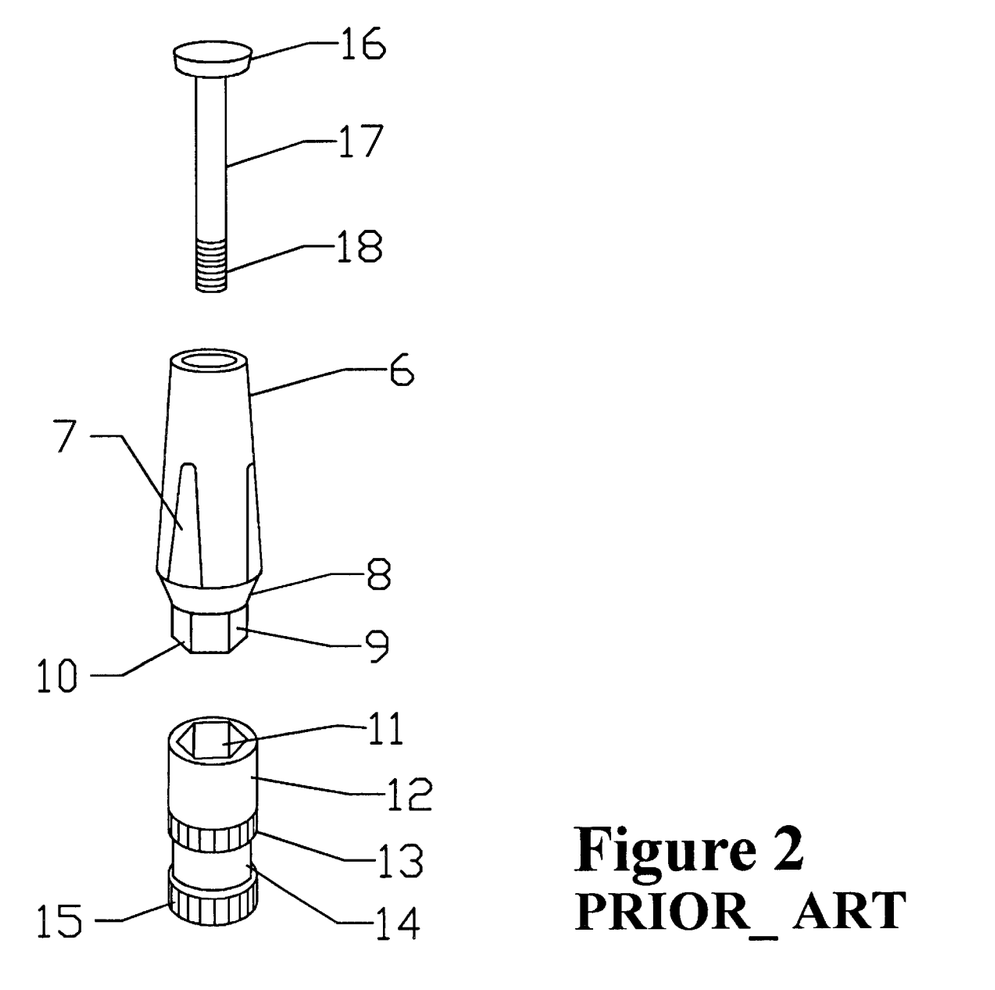
FIG. 2 (prior art) shows a typical conic impression post.

FIGS. 1 and 2 inclusive are included as reference from prior application Ser. No. 09/309,477, now allowed. FIG. 2 has been modified to better represent a typical prior art apparatus. FIGS. 3 through 9 illustrate the subject matter of this application.

A DETAILED DESCRIPTION OF THE DRAWINGS

An accurate model can be simultaneously fabricated from an impression of the upper and lower jaws with remaining natural teeth and dental implants by means of a triple tray. FIG. 1 shows a typical molded plastic anterior triple tray with handle 1, curved outer dam wall 2 and horizontal open mesh 3. A quick setting polymer paste is placed in an arc on both upper and lower sides of the mesh 3 against the inner dam wall 4. The dentist places the triple tray in the patient's mouth and closes the jaw in a natural occluded, centric position. The thin loose mesh conforms to the touching occlusal surfaces of the upper and lower teeth while the polymer completely enfolds the teeth, implants and other structures to form an accurate impression. A plastic, lingual side dam molded to the mesh can be present but is not shown in this drawing.

A typical prior art, impression post, detailed in FIG. 2, consists of a metal cylindrical or conic body having flats 7 to prevent rotation when imbedded in the elastomeric impression. Soft tissue emergence taper 8 and collar 9 can mimic the profile of the permanently installed abutment used to secure the final prostheses. An external hex pattern 10 with facets 9 is used to clock or radially align the impression post within the internal hex 11 of a dental implant (not shown) and the implant analog post 12 (shown). This assures proper clocking or radial alignment. Knurled regions 13 and 15 and undercut region 14 securely lock the implant analog post in the plaster replica of the mouth region being modeled. Retaining screw 17 has a wide head 16 acting to positively lock the impression transfer post 6 within the elastomeric mold by means of a positive snap or detent. This snap is distinctly felt as the impression transfer post is reseated firmly in the elastomeric mold. Screw threads 18 mate with internal threads within the implant fixture analog 12.

The improvements in the present invention further shorten the number of steps necessary to form a complete model of the mouth structures while improving dimensional accuracy by leaving an impression cap intimately embedded within the cured elastomeric compound and providing the cap with a close-fitting, snap-action recess mating to a short impression post.

Figure 5:
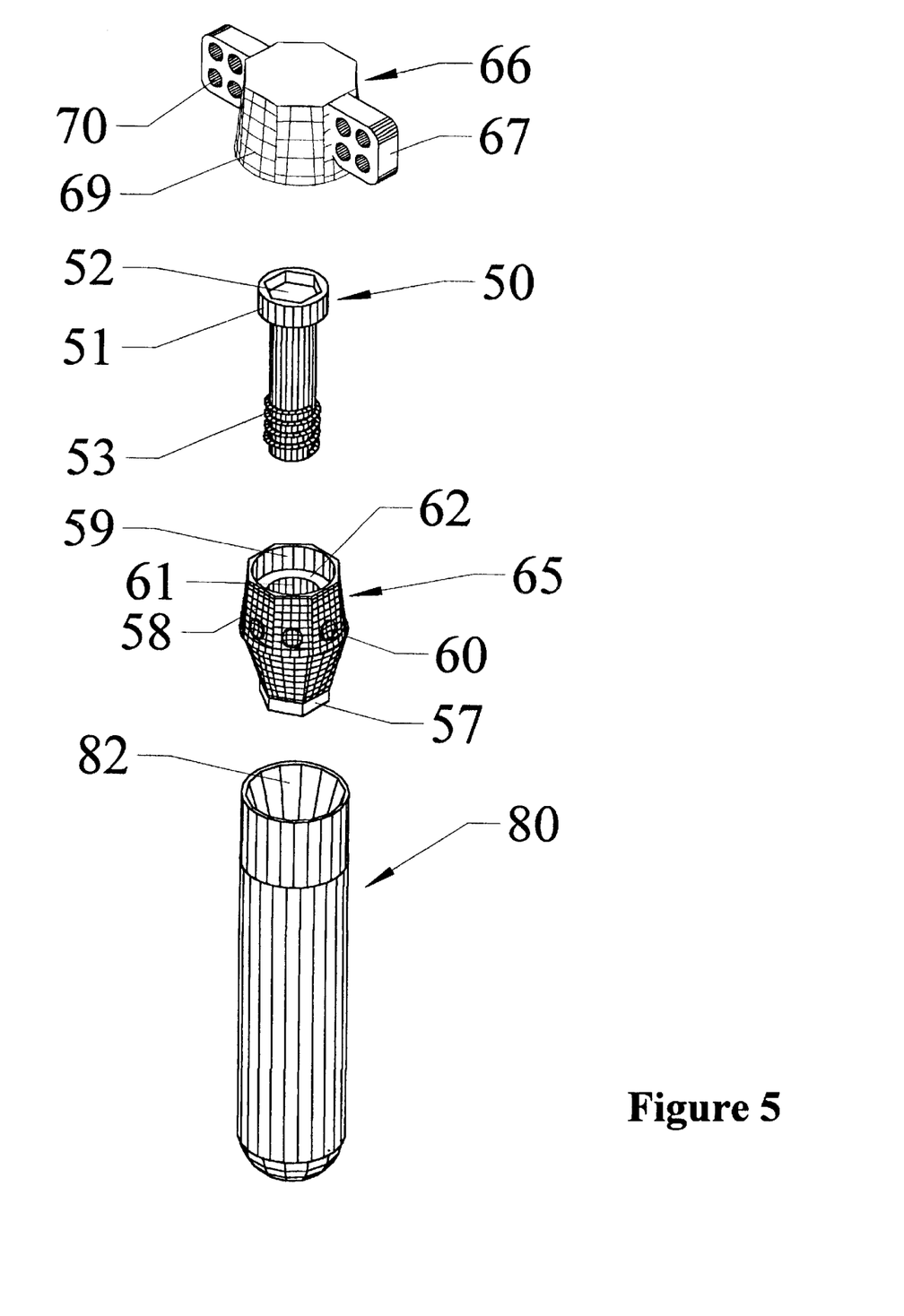
FIG. 5 is a perspective drawing of a reduced height impression cap socket with crossbar wings, mounting screw, mating impression post and implant.

FIG. 5 details an exploded view of a typical permanent endo-osseal implant 80 having a lower rounded end and an conical recess 82 in the upper end with a recessed alignment hexagonal pattern and a threaded coaxial hole. The internal taper and hexagonal lock are known to the art. The low-profile, alignment transfer post 65 with a lower hexagonal protrusion 57 mates and clocks with the recessed hexagonal pattern in the implant 80. The exposed coronal, lateral surfaces consist of facets 58 of a truncated pyramid. In this example, the facets form an octagonal truncated prism. At least one dimple 60 on at least one facet 58 provides a positive lock when a mating with a matching projection in a recess located under the impression cap 66. Recess 59 and axial through-hole 61 as well as countersink 62 allow the threaded shaft 53 of a cap-screw type machine screw 50 to retain the alignment post without adding to the assembled height above the soft tissue line. Cap screw 50 is equipped with a hexagonal recess 52 to accommodate a wench for assembly and removal of the impression post to the implant and then the implant analog.

Figure 6:
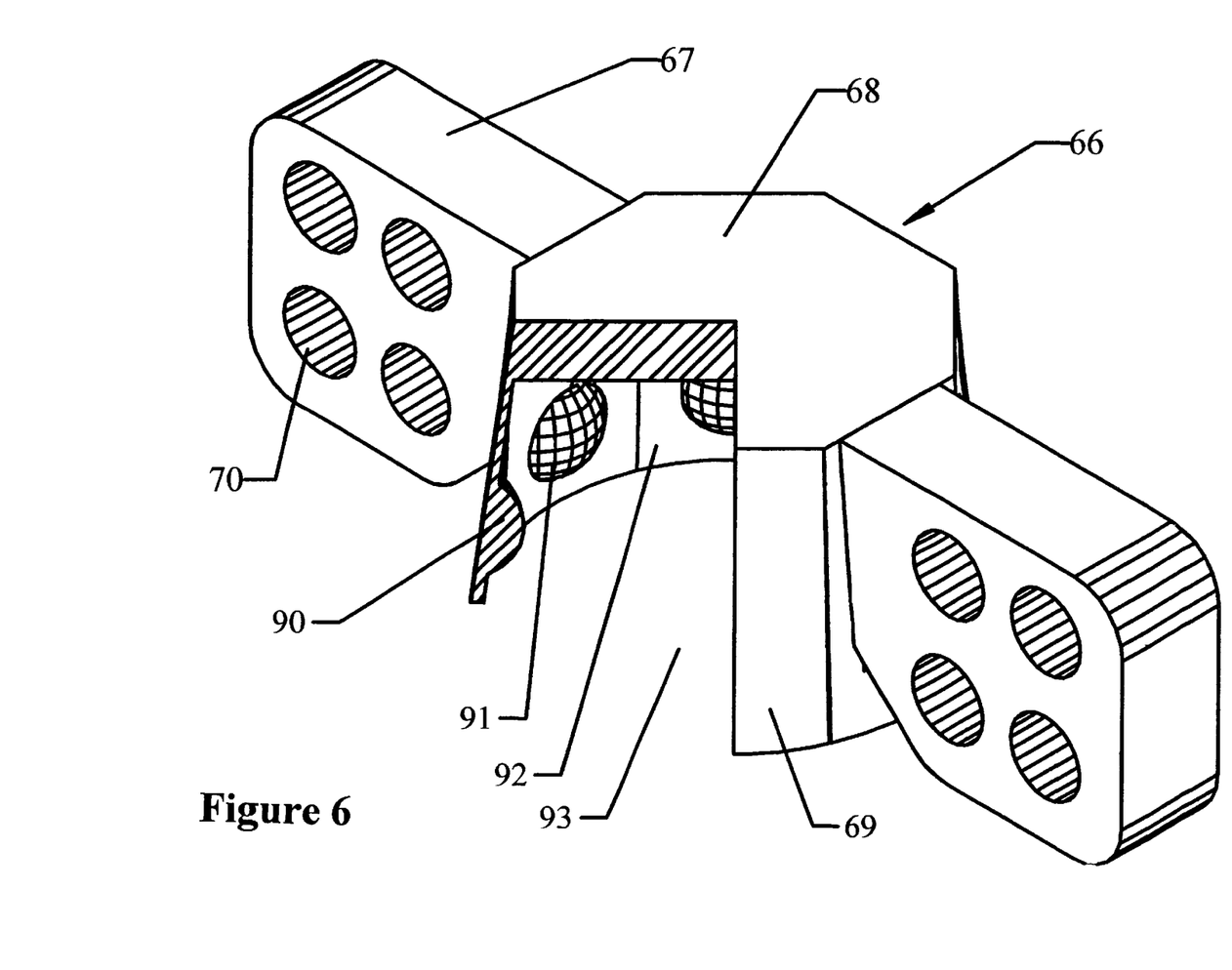
FIG. 6 is a sectioned perspective of an eight sided, impression cap with a locking projections.

The impression cap 66 is shown in detail in FIG. 6 with a pyramidal body having a truncated prismatic internal recess 93 that slip-fits and snaps upon the impression transfer post 65. Low profile projections or wings 67 having through-holes, slots or deep recesses 70 act to anchor the impression cap 66 within the embedding compound. The impression cap with the surrounding cured elastomer can be snapped free of the low profile impression post 65 after compound has cured to a firm rubbery mass. The impression post machine cap screw 50 is removed and the impression post is then mounted to an implant post analog with the same screw. The impression post 65 is then snapped back into the impression cap 66. In this manner, the implant analog has the same orientation as the permanent implant. A stone cast is then made retaining the analog.

Figure 3:
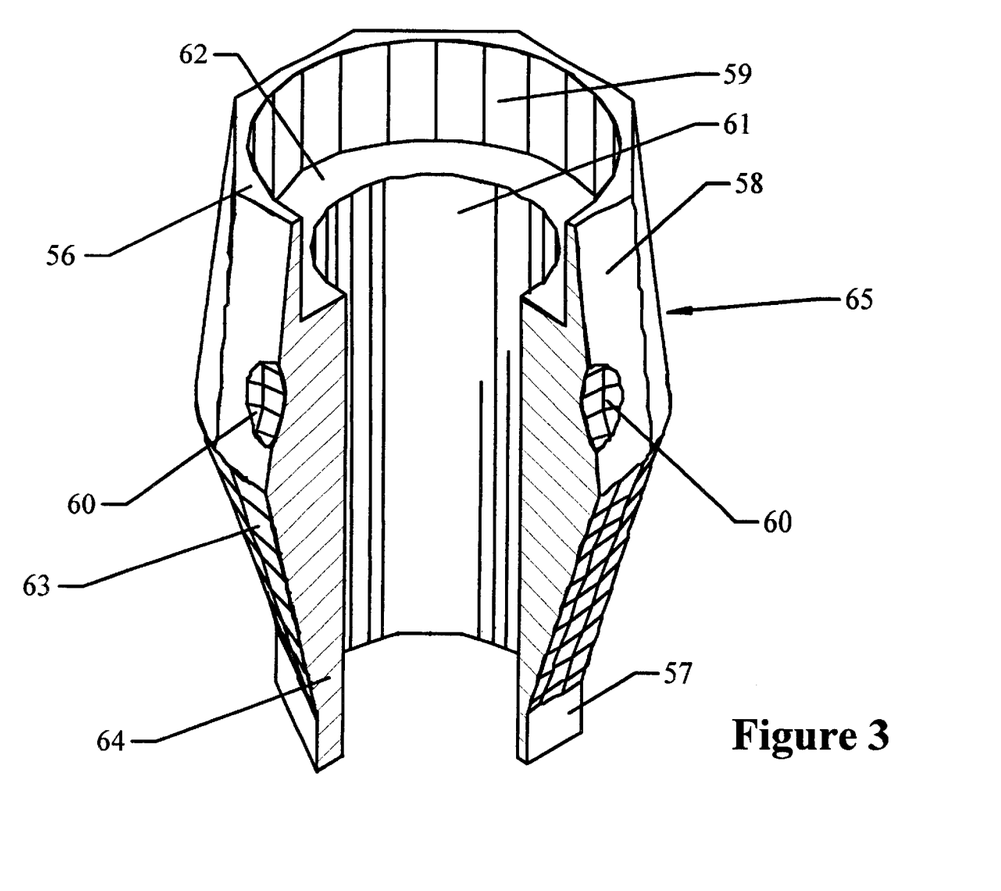
FIG. 3 shows a sectioned, low profile alignment post.

FIG. 3 offers a detailed, sectioned view of the low profile impression post 65. Quarter section 64 is removed. Recess 59 with flat 62 accommodates the head of a machine screw. Axial, through-hole 61 provides access for the mounting screw to hold the impression post to the mating implant.

Tapered surfaces 58 match a tapered recess in a mating impression cap. Dimples or recessed detents 60 act to positively lock the impression cap to the impression post while still allowing for easy removal. An audible and tactile snap is felt when the impression cap and mating impression post are properly engaged. Tapered section 63 and hexagonal projection 57 are shown to illustrate known methods of clocking and locking in firm position the implant post within the mating implant and implant analog. The hexagonal base 57 in combination with the octagonal top 56 of the impression post offer a sufficient number of clocking positions for all applications.

Figure 4:
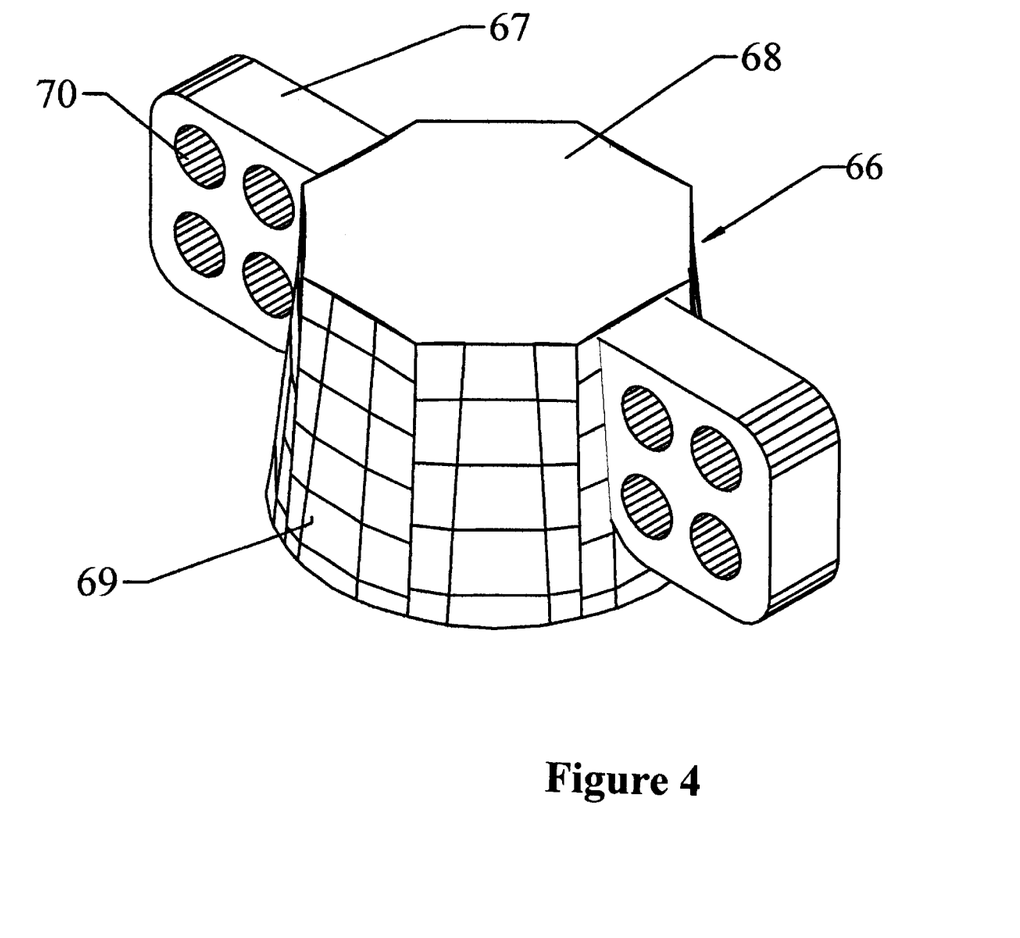
FIG. 4 show a perspective, view of an implant, reduced height, transfer post cap.

FIG. 4 shows a perspective view of the impression cap 66 with wings 67 and through-holes, vents or slots 70 act to lock the cap firmly and accurately within the elastomeric embedding compound.

Octagonal top 68 and tapered sides 69 along with the side mounted wings 67 have a low profile that do not project into the occlusal plane or interfere with the complete centric closure.

FIG. 6 is a cut-away perspective view of the impression cap 65 illustrating projections 91 with cross-section 90 that snap into recessed mating dimples 60 on the impression post 65.

Figure 7:
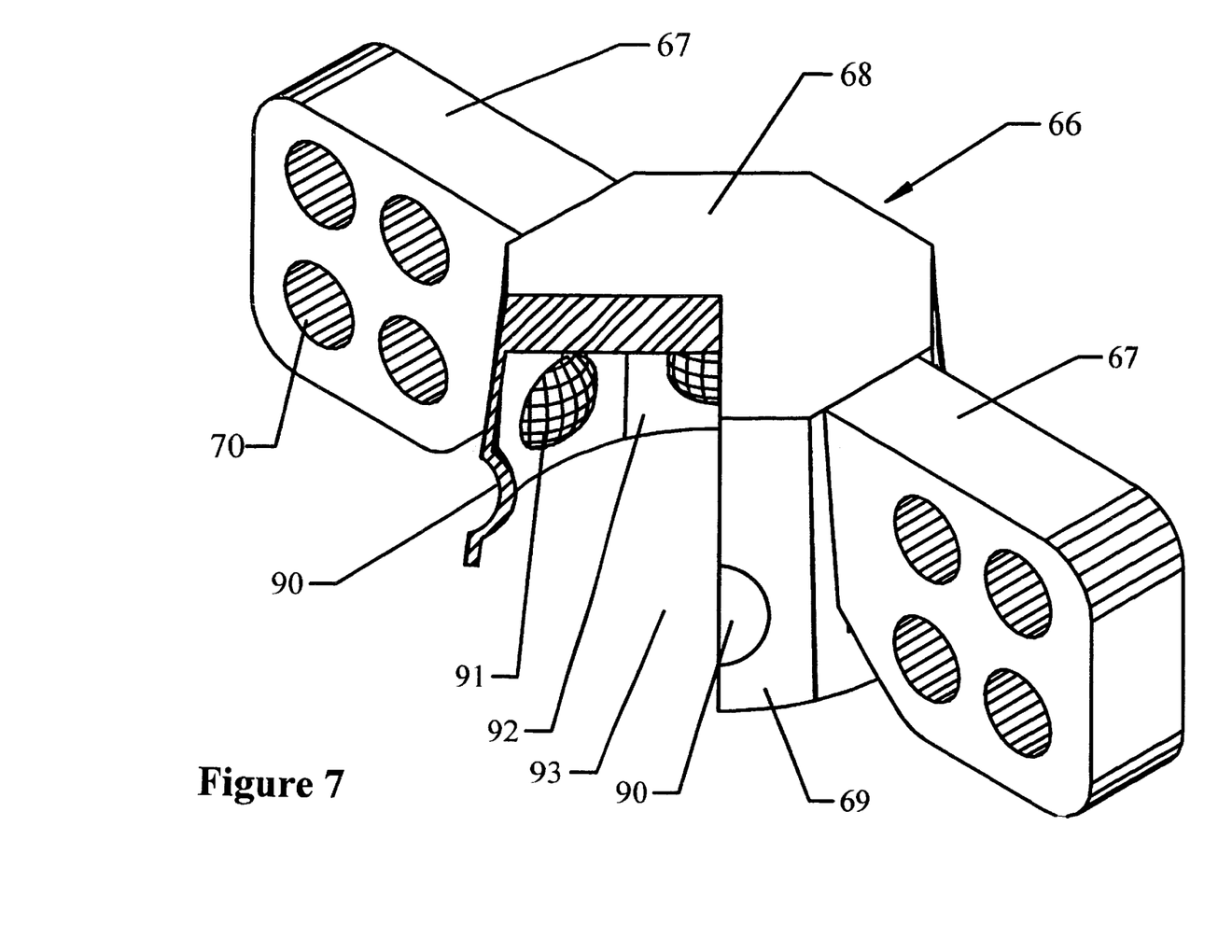
FIG. 7 is a sectioned perspective of an eight sided, impression cap thin walled, snap locking projections.

FIG. 7 is a cut away perspective view of the impression cap 66 with projections 91 shown with thin-walled cross-section 90. These flexible inward projections snap easily and firmly into matching dimples 60 on the impression post. A positive snapping sound is heard and felt when the cap is properly seated. Internal surfaces 92 match the outer octagonal tapered facets 58 on the impression post. The drawing exaggerates the height of these projections for clarity. Fewer projections can be molded without loss of alignment. The impression post should be equipped with a full set of dimples to allow the impression cap to clock to each of eight positions. Alternative numbers of sides for the tapered, truncated prism other than eight are anticipated by this invention.

Figure 8:
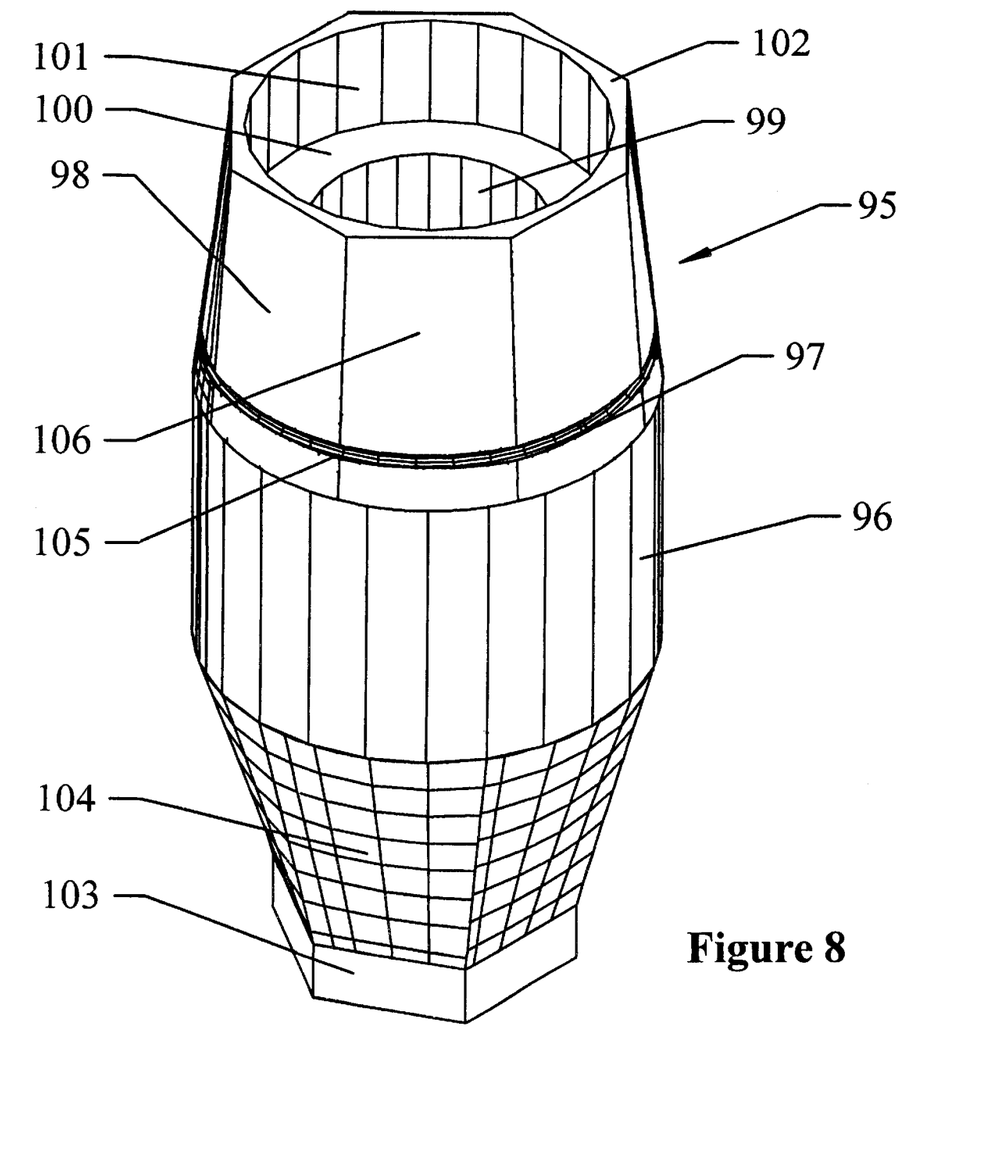
FIG. 8 is a perspective view of an impression post with circumferential locking groove and barrel extension.
Figure 9:
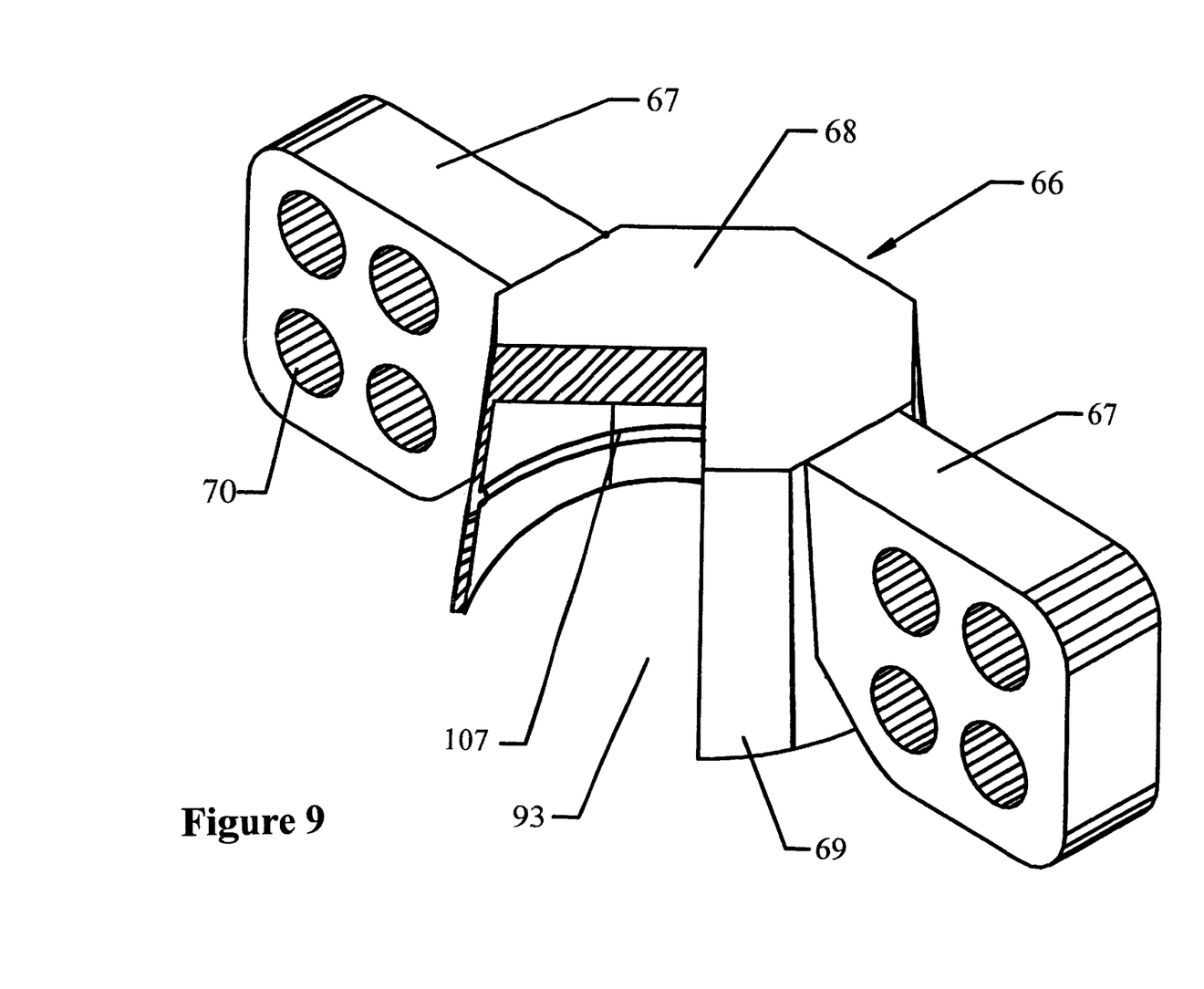
FIG. 9 is a sectioned view of an impression transfer cap with an internal circumferential rib.

FIG. 8 offers another example of an implant impression post 95 with an added circumferential groove 97 in the tapered faces of truncated pyramid 102. This groove snap locks with a matching projection in the recessed underside of the impression cap 107 as detailed in FIG. 9. This groove need only to notch the edge of mating surfaces represented by 98 and 106 to be effective. Recess 101 with flat 100 and axial, through-hole 99 allow a machine screw to hold the impression post in place. In this embodiment of the invention, this implant post illustrates an extended portion of the barrel 96 for implants located further below the soft tissue line. Alignment taper 104 and hex pattern 103 are illustrated as known methods of clocking and locking the impression post to the mating implant and implant analog. Impression caps are designed to be manufactured from dimensionally stable resilient plastic compounds.

What is claimed is:

1. A dental implant registration apparatus comprising:
   an impression post having
      a lower, implant-compatible, clocking and locking means;
   a tapered, truncated, pyramidal upper region having external faces with at least one dimpled detent on at least one of said external faces; and
   a top surface with a counter-sunk, axial, through-hole for an implant-compatible mounting machine screw;
   a machine screw;
   and a low profile impression cap with perforated side-wings and with a tapered, truncated, pyramidal lower recess matching to said tapered truncated, pyramidal, upper region of said impression post said pyramidal lower recess having internal faces, wherein at least one of said internal faces include at least one projection to match and snap-lock into said at least one dimpled detent.

2. A dental implant registration apparatus comprising:
an impression post having
- a lower, implant-compatible, clocking and locking means;
- a tapered, truncated, pyramidal upper region having external faces with a circumferentially, radially grooved detent on the external faces; and
- a top surface with a counter-sunk, axial, through-hole for an implant-compatible mounting machine screw;

a machine screw;

and a low profile impression cap with perforated side-wings and with a tapered, truncated, pyramidal lower recess matching to said tapered truncated, pyramidal, upper region of said impression post, said pyramidal lower recess having internal faces, said internal faces having projections to match and snap-lock into said circumferentially, radially grooved detent.

* * * * *